US008580505B2

(12) United States Patent
Wang et al.

(10) Patent No.: US 8,580,505 B2
(45) Date of Patent: Nov. 12, 2013

(54) FAST PCR FOR STR GENOTYPING

(75) Inventors: Dennis Wang, Dublin, CA (US); Lori Hennessy, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 124 days.

(21) Appl. No.: 13/035,849

(22) Filed: Feb. 25, 2011

(65) Prior Publication Data

US 2011/0212446 A1    Sep. 1, 2011

Related U.S. Application Data

(60) Provisional application No. 61/308,862, filed on Feb. 26, 2010.

(51) Int. Cl.
*C12Q 1/68* (2006.01)
*C12P 19/34* (2006.01)

(52) U.S. Cl.
USPC ........................ 435/6.12; 435/6.1; 435/6.11

(58) Field of Classification Search
None
See application file for complete search history.

(56) References Cited

U.S. PATENT DOCUMENTS

| | | | |
|---|---|---|---|
| 4,889,818 | A | 12/1989 | Gelfand et al. |
| 5,436,149 | A | 7/1995 | Barnes et al. |
| 2001/0000752 | A1 | 5/2001 | Franzen |
| 2003/0096277 | A1 | 5/2003 | Chen |
| 2003/0186312 | A1 * | 10/2003 | Uemori et al. ........... 435/6 |

FOREIGN PATENT DOCUMENTS

| | | |
|---|---|---|
| EP | 0469610 A1 | 2/1992 |
| KR | 10-0277289 B1 | 12/2000 |
| WO | 2006/074233 A2 | 7/2006 |
| WO | 2009/059049 A1 | 5/2009 |

OTHER PUBLICATIONS

Butler et al., "A novel multiplex for simultaneous amplification of 20 Y chromosome STR markers," Forensic Science International, 2002, vol. 129, pp. 10-24.*
Yang et al., "Rapid Prenatal Diagnosis of Trisomy 21 by Real-time Quantitative Polymerase Chain Reaction with Amplification of Small Tandem Repeats and S100B in Chromsome 21," Yonsei Medical Journal, 2005, vol. 46, No. 2, pp. 193-197.*
Butler et al., "Quality control of PCR primers used in multiplex STR amplification reactions," Forensic Science International, 2001, vol. 119, pp. 87-96.*
Gaines et al., "Reduced Volume PCR Amplification Reactions Using the AmpFISTR® Profiler Plus™ Kit," J. Forensic Sci, Nov. 2002, vol. 47, No. 6, pp. 1-14.*
Giese, Heidi et al. "Fast Multiplexed Polymerase Chain Reaction for Conventional and Microfluidic Short Tandem Repeat Analysis", *J. Forensic Sci.*, vol. 54, No. 6, Nov. 2009, pp. 1287-1296.
Saiki, Randall K. et al. "Primer-Directed Enzymatic Amplification of DNA with a Thermostable DNA Polymerase", *Science*, vol. 239 Jan. 29, 1988, pp. 487-491.
Vallone, Peter M. et al. "Demonstration of rapid multiplex PCR amplification involving 16 genetic loci", *Forensic Science International: Genetics*, vol. 3, 2008, pp. 42-45.
Gao, Q. et al. Simultaneous genetic typing from multiple short tandem repeat loci using a 96-capillary array electrophoresis system. Electrophoresis, vol. 20, No. 7, pp. 1518-1526 (1999).
Puers, C. et al. Identification of repeat sequence heterogeneity at the polymorphic short tandem repeat locus HUMTH01[AATG]n and reassignment of alleles in population analysis by using a locus-specific allelic ladder., Am. J. Hum. Genet. vol. 53, No. 4, pp. 953-958 (1993).
Wang, D. et al. Rapid STR Analysis of single source DNA samples in 2 h., Forensic Science Intl: Genetics Supplement Series, vol. 2, No. 1, pp. 115-116 (2009).
Laurin, N. et al., "Optimization and Validation of a Fast Amplification Protocol for AmpFISTR1 Profiler Plus1 for Rapid Forensic Human Identification", *Forensic Science International; Genetics*, vol. 6, Issue 1, Elsevier Ireland Ltd., Jan. 2012, 47-57.
Yoshida, K. et al., "Improvement of Polymerase Chain Reaction Condition to Detect Polymorphic Dinucleotide Repeat Microsatellite DNA Marker in the Puffer Fish Fugu Rubripes", *Fisheries Science*, vol. 66, Issue 2,, Apr. 2000, 397-399.
Braithwaite, D K. et al., "Compilation, alignment, and phylogenetic relationships of DNA polymerases", *Nucleic Acids Research*, vol. 21, No. 4, Feb. 25, 1993, 787-802.
Collins, P. J. et al., "Developmental validation of a single-tube amplification of the 13 CODIS STR loci, D2S1338, D19S433, and amelogenin: The AmpFISTR Identifiler PCR amplification kit", *Journal of Forensic Sciences*, vol. 49, No. 6, 2004, 1265-1277.
EP11748195.2, , "Extended European Search Report", Aug. 5, 2013, 11 pages.
PCT/US2011/026351, , "International Preliminary Report on Patentability", Aug. 28, 2012, 5 pages.
PCT/US2011/026351, , "Notification of Transmittal of the International Search Report and the Written Opinion of the International Searching Authority, or the Declaration", Dec. 21, 2011, 10 Pages.

* cited by examiner

*Primary Examiner* — Young J Kim

(57) ABSTRACT

Disclosed is a method of amplifying a nucleic acid sequence, wherein the method comprises subjecting a reaction mixture to at least one amplification cycle, wherein the reaction mixture comprises a double-stranded nucleic acid and at least two primers capable of annealing to complementary strands of the double-stranded nucleic acid and amplifying at least one short tandem repeat (STR) using a Family A DNA polymerase in a Fast PCR protocol having a two-step amplification cycle in 25 seconds or less. Also disclosed are real-time PCR methods using the two-step protocol and kits for STR profiling using the Fast PCR protocol.

16 Claims, 5 Drawing Sheets

FAST PCR FOR STR GENOTYPING

CROSS-REFERENCE TO RELATED APPLICATIONS

This application claims priority to U.S. application No. 61/308,862, filed Feb. 26, 2010, the disclosure of which is herein incorporated by reference in its entirety.

FIELD

In general, the present teachings relate to the amplification of a nucleic acid sample for the purposes of obtaining an STR profile in less than 45 minutes.

BACKGROUND

Since the PCR process depends greatly on the performance of the DNA polymerase used, various DNA polymerases have been searched for in nature or re-engineered in vitro. Two key properties of a DNA polymerase play important roles in determining the overall reaction time required for the PCR amplification. The first property is "elongation rate" (or "extension rate"), which is defined as the number of nucleotides polymerized per second per molecule of DNA polymerase. The second property is "processivity", which is defined as the average number of nucleotides added by a DNA polymerase in a single binding event. Both "elongation rate" and "processivity" depends on the components of the reaction media and on the DNA template sequence.

Rapid and accurate detection of DNA profiles is a key aspect of forensic sample analysis and the technique of polymerase chain reaction (PCR) plays an integral part in this process. Methods to decrease the PCR time will save on technician labor. There is an unmet need to decrease PCR time without compromising sensitivity, specificity and accuracy of results.

SUMMARY OF SOME EMBODIMENTS OF THE INVENTION

In some embodiments, disclosed is a method for amplifying a nucleic acid sequence wherein the method involves subjecting a reaction mixture to at least one amplification cycle, wherein the reaction mixture comprises a double-stranded nucleic acid, at least two primers capable of annealing to complementary strands of the double-stranded nucleic acid and amplifying at least one short tandem repeat (STR), and a Family A DNA polymerase, and wherein the at least one amplification cycle comprises denaturing the double-stranded nucleic acid in the reaction mixture; and annealing the at least two primers to complementary strands of the denatured double-stranded nucleic acid and extending the at least two primers; and wherein the time to complete one amplification cycle is 25 seconds, 20 seconds, 15 seconds, 10 seconds or less.

In some embodiments the annealing temperature in the amplification cycle is at least about 5° C. greater, 10° C. greater, or 15° C. greater than the predicted Tm of at least one of the at least two primers while the annealing temperature ranges from about 55° C. to about 75° C. and the annealing and extending occur at the same temperature. In some embodiments the reaction mixture is held at the annealing temperature for 1 second, 2 seconds, 3 seconds or up to 20 seconds or more. In some embodiments the denaturing temperature is from 4 to 8 seconds and the annealing temperature in conjunction with the extending temperature is from 5 seconds to 25 seconds.

In some embodiments, the DNA polymerase used in the Fast PCR protocol herein is a Family A (Pol A) DNA polymerase from either a natural or recombinant source including fragments and variants thereof.

In some embodiments, the Fast PCR protocol method as taught herein can be used for the amplification of a nucleic acid sample to obtain an STR profile in 45 minutes or less. In other embodiments a multiplex of at least 15 STR loci, at least 20 STR loci or at least 40 STR loci plus the amelogenin loci are amplified by the Fast protocol method. In some embodiments, the Fast PCR protocol method is used for a real-time PCR reaction.

In other embodiments, kits are taught in varying configurations for use in human identification comprising at least one primer pair for the amplification of an STR loci in an amplification cycle of 25 seconds or less.

DESCRIPTION OF EXEMPLARY EMBODIMENTS

Figure 1A:
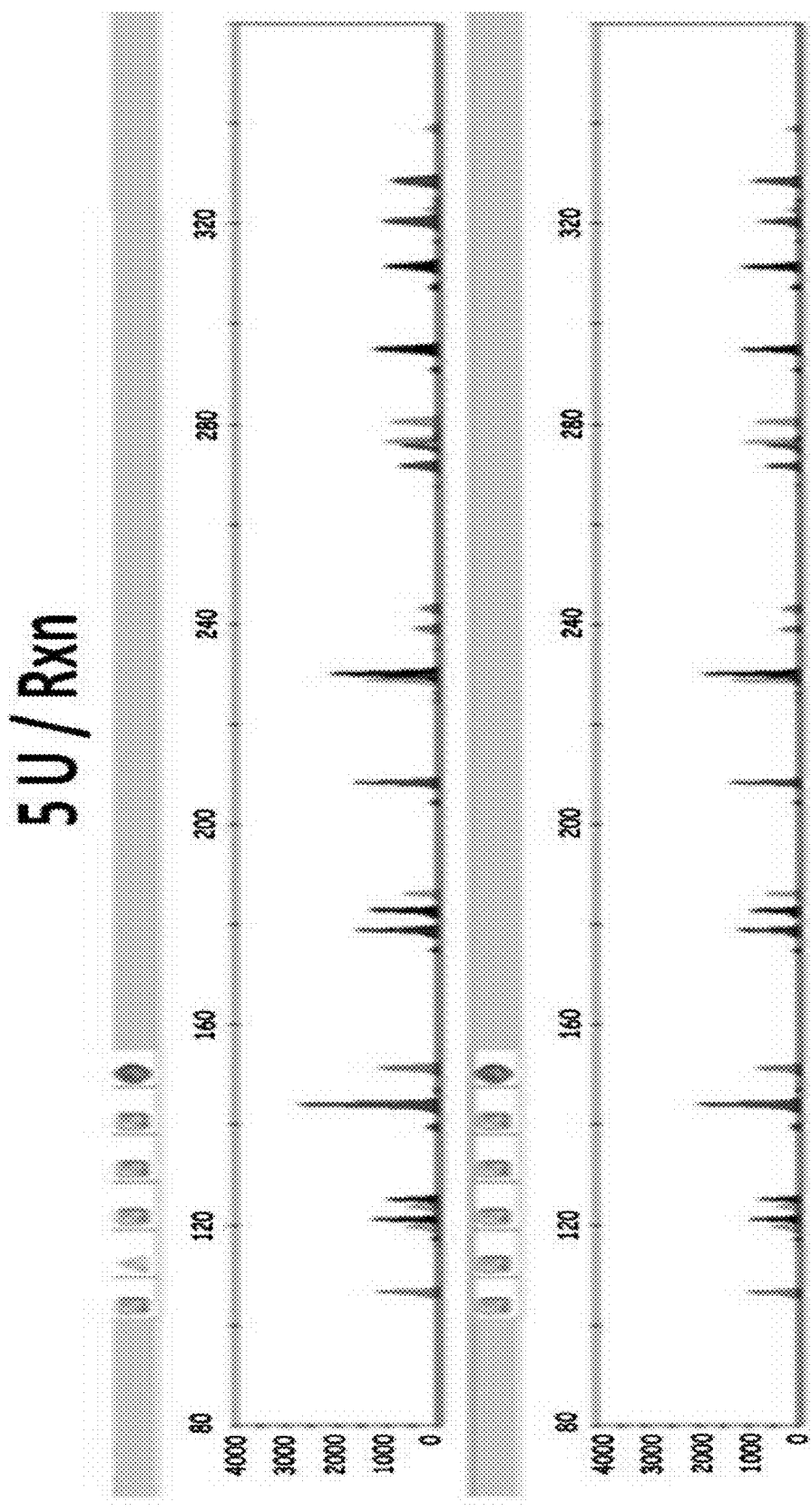
FIGS. 1A-1E are schematics depicting results in replicate of an enzyme titration experiment using Platinum® Taq and the Fast PCR protocol.

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, 5th Ed., W. H. Freeman Pub., New York, N.Y. all of which are herein incorporated in their entirety by reference for all purposes.

As used herein, "amplify" refers to the process of enzymatically increasing the amount of a specific nucleotide sequence. This amplification is not limited to but is generally accomplished by PCR. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions.

As used herein, the term "amplifying" refers to a process whereby a portion of a nucleic acid is replicated using, for example, any of a broad range of primer extension reactions. Exemplary primer extension reactions include, but are not limited to, PCR. Unless specifically stated, "amplifying" refers to a single replication or to an arithmetic, logarithmic, or exponential amplification.

As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur.

The terms "amplification cycle" and "PCR cycle" are used interchangeably herein and as used herein refers to the denaturing of a double-stranded polynucleotide sequence followed by annealing of a primer sequence to its complementary sequence and extension of the primer sequence.

The terms "amplicon," "amplification product" and "amplified sequence" are used interchangeably herein and refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" and "amplified sequence" includes products from any number of cycles of amplification reactions.

As used herein, the terms "amplification primer" and "oligonucleotide primer" are used interchangeably and refer to an oligonucleotide, capable of annealing to an RNA or DNA region. The region annealed to can be adjacent a target sequence, including but not limited to a SNP, a STR or mutation region, and serving as an initiation primer for DNA synthesis under suitable conditions well known in the art. Typically, a PCR reaction employs an "amplification primer pair" also referred to as an "oligonucleotide primer pair" including an "upstream" or "forward" primer and a "downstream" or "reverse" primer, which delimit a region of the RNA or DNA to be amplified. A first primer and a second primer may be either a forward or reverse primer respectively, and are used interchangeably herein and are not to be limiting.

As used herein, "extension" refers to the amplification cycle after the primer oligonucleotide and target nucleic acid have annealed to one another, wherein the polymerase enzyme catalyzes primer extension, thereby enabling amplification, using the target nucleic acid as a replication template.

As used herein, the terms "polynucleotide", "oligonucleotide", and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted. The letters A, C, G, and T can be used to refer to the bases themselves, to nucleosides, or to nucleotides comprising the bases, as is standard in the art. In naturally occurring polynucleotides, the inter-nucleoside linkage is typically a phosphodiester bond, and the subunits are referred to as "nucleotides."

When two different, non-overlapping oligonucleotides anneal to different regions of the same linear complementary nucleic acid sequence, the 3' end of one oligonucleotide points toward the 5' end of the other; the former may be called the "upstream" oligonucleotide and the latter the "downstream" oligonucleotide.

The terms "polymerase" and "nucleic acid polymerase" are used interchangeably and as used herein refer to any polypeptide that catalyzes the synthesis or sequencing of a polynucleotide using an existing polynucleotide as a template.

As used herein, "DNA polymerase" refers to a nucleic acid polymerase that catalyzes the synthesis or sequencing of DNA using an existing polynucleotide as a template.

As used herein, "Thermostable DNA polymerase" refers to a DNA polymerase that, at a temperature higher than 37° C., retains its ability to add at least one nucleotide onto the 3' end of a primer or primer extension product that is annealed to a target nucleic acid sequence. In certain embodiments, a thermostable DNA polymerase remains active after exposure to a temperature greater than about 37° C. In certain embodiments, a thermostable DNA polymerase remains active at a temperature greater than about 42° C. In certain embodiments, a thermostable DNA polymerase remains active at a temperature greater than about 50° C. In certain embodiments, a thermostable DNA polymerase remains active at a temperature greater than about 60° C. In certain embodiments, a thermostable DNA polymerase remains active at a temperature greater than about 70° C. In certain embodiments, a thermostable DNA polymerase remains active at a temperature greater than about 80° C. In certain embodiments, a thermostable polymerase remains active at a temperature greater than about 90° C.

As used herein, "nucleoside" includes the natural nucleosides, including 2'-deoxy and 2'-hydroxyl forms, e.g. as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990); or the like. Such analogs include synthetic nucleosides designed to enhance binding properties, reduce degeneracy, increase specificity, and the like.

The terms "elongation rate" and "extension rate" are used interchangeably herein and as used herein refer to the number of nucleotides polymerized per second per molecule of DNA polymerase.

The term "processivity" as used herein refers to the average number of nucleotides added by a DNA polymerase in a single binding event.

The term "terminal transferase activity" as used herein refers to the non-templated addition of a single nucleotide, mainly adenosine, to the 3' end of the amplified DNA strand.

As defined herein, "5'→3' nuclease activity" or "5' to 3' nuclease activity" refers to that activity of a template-specific nucleic acid polymerase including either a 5'→3' exonuclease activity traditionally associated with some DNA polymerases whereby nucleotides are removed from the 5' end of an oligonucleotide in a sequential manner, (i.e., *E. coli* DNA polymerase I has this activity whereas the Klenow fragment does not), or a 5'→3' endonuclease activity wherein cleavage occurs more than one nucleotide from the 5' end, or both.

As used herein, the phrase "thermostable" and "thermally stable" are interchangeable.

As used herein, the term "thermostable nucleic acid polymerase" refers to an enzyme which is relatively stable to heat when compared, for example, to nucleotide polymerases from *E. coli* and which catalyzes the polymerization of nucleosides. Generally, the enzyme will initiate synthesis at the 3'-end of the primer annealed to the target sequence, will proceed in the 5'-direction along the template and if possessing a 5' to 3' nuclease activity, hydrolyzing intervening, annealed probe to release both labeled and unlabeled probe fragments, until synthesis terminates. A representative thermostable enzyme isolated from *Thermus aquaticus* (Taq) is described in U.S. Pat. No. 4,889,818 and a method for using it in conventional PCR are described in Saiki et al., (1988), Science 239:487.

Exemplary bacteria from which the DNA Pol A polymerase can be isolated include but are not limited to *Thermus aquaticus, Thermus thermophilus, Thermatoga maritime, Bacillus caldotenax, Carboxydothermus hydrogenformans, Thermoanaerobacter thermohydrosulfuricus, Thermus brokianus, Thermus caldophilus GK24, Thermus flavus, Thermus rubens*, or a mutants of any of the aforementioned thereof.

As used herein "hot-start" refers to the thermal exposure of a reaction solution, often a PCR reaction mix, to a temperature sufficient to restore enzymatic activity, i.e., thermal reactivation of a DNA polymerase which had been inactivated by, for example, chemical or antibody means.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/ RNA heteroduplexes or to duplex cDNA by methods known to one of skill in the art. The PCR method also includes reverse transcriptase-PCR and other reactions that follow principles of PCR.

The term "primer" refers to a polynucleotide (oligonucleotide) and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides (dNTPs) and the like.

The term "primer extension" as used herein refers to both to the synthesis of DNA resulting from the polymerization of individual nucleoside triphosphates using a primer as a point of initiation, and to the joining of additional oligonucleotides to the primer to extend the primer. As used herein, the term "primer extension" is intended to encompass the ligation of two oligonucleotides to form a longer product which can then serve as a target in future amplification cycles. As used herein, the term "primer" is intended to encompass the oligonucleotides used in ligation-mediated amplification processes which are extended by the ligation of a second oligonucleotide which hybridizes at an adjacent position.

As used here, the term "primer extension reaction" refers to a reaction in which a polymerase catalyzes the template-directed synthesis of a nucleic acid from the 3' end of a primer. The term "primer extension product" refers to the resultant nucleic acid. A non-limiting exemplary primer extension reaction is the polymerase chain reaction (PCR). The terms "extending" and "extension" refer to the template-directed synthesis of a nucleic acid from the 3' end of a primer, which is catalyzed by a polymerase.

The term "nucleic acid sequence" as used herein can refer to the nucleic acid material itself and is not restricted to the sequence information (i.e. the succession of letters chosen among the five base letters A, C, G, T, or U) that biochemically characterizes a specific nucleic acid, for example, a DNA or RNA molecule. Nucleic acids shown herein are presented in a 5'→3' orientation unless otherwise indicated.

The term "Tm" as used herein refers to the melting temperature at which half of the DNA strands in the double-stranded state and half are in the single-stranded state.

The term "denaturing" as used herein refers to separation of a double-stranded nucleic acid into single, complementary strands. Most often, hydrogen bonds are broken to accomplish denaturing using either heat or chemical methods such as urea.

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The terms "complement" and "complementary" as used herein refer to the ability of two single stranded polynucleotides (for instance, a primer and a target polynucleotide) to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary.

The term "extending" as used herein refers to increasing the primer sequence length in a 5' to 3' direction thereby forming an amplicon polynucleotide complementary to the target sequence The terms "detecting" and "detection" are used in a broad sense herein and encompass any technique by which one can determine the presence of or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products. In other embodiments detecting can be achieved through measuring the size of a nucleic acid amplification product.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, mRNA, siRNA, miRNA, shRNA, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

As used herein, the term "short tandem repeat (STR) loci" refers to regions of a genome which contains short, repetitive sequence elements of 2 to 7 base pairs in length. Each sequence element is repeated at least once within an STR and is referred to herein as a "repeat unit." The term STR also encompasses a region of genomic DNA wherein more than a single repeat unit is repeated in tandem or with intervening bases, provided that at least one of the sequences is repeated at least two times in tandem. Examples of STRs, include but are not limited to, a triplet repeat, e.g., ATC in tandem; a 4-peat (tetra-repeat), e.g., GATA in tandem; and a 5-peat (penta-repeat), e.g., ATTGC in tandem and so on. Information about specific STRs that can be used as genetic markers can be found in, among other places, the STRbase at www.cstl.nist.gov/strbase.

The term "detectable signal" as used herein refers to a signal that is capable of being detected under certain conditions. In certain embodiments, a detectable signal is detected when it is present in a sufficient quantity.

The term "signal moiety" as used herein refers to a moiety that is capable of producing a detectable signal.

The term "indicator molecule" as used herein refers to a molecule comprising a label that can be detected.

The term "probe" as used herein refers to a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled. The probe can be an oligonucleotide that is complementary to at least a portion of an amplification product formed using two primers.

The term "indicator probe" as used herein refers to a probe comprising a label that can be detected.

The term "5'-nuclease probe" as used herein refers to a probe that comprises a signal moiety linked to a quencher moiety or a donor moiety through a short oligonucleotide link element. When the 5'-nuclease probe is intact, the quencher moiety or the donor moiety influences the detectable signal from the signal moiety. According to certain embodiments, the 5'-nuclease probe selectively hybridizes to a target nucleic acid sequence and is cleaved by a polypeptide having 5' to 3' exonuclease activity, e.g., when the probe is replaced by a newly polymerized strand during a primer extension reaction, such as PCR.

As used herein "quencher moiety" refers to a moiety that causes the detectable signal of a signal moiety to decrease when the quencher moiety is sufficiently close to the signal moiety.

Also herein, the recitations of numerical ranges by endpoints include all numbers subsumed within that range (e.g., 1 to 5 includes 1, 1.5, 2, 2.75, 3, 3.80, 4, 5, etc.).

Reference will now be made to various embodiments, examples of which are illustrated in the accompanying drawings.

DNA polymerases are known to those skilled in the art. DNA polymerases include DNA-dependent polymerases, which use DNA as a template, or RNA-dependent polymerases, such as reverse transcriptase, which use RNA as a template.

Based on sequence homology, bacterial DNA polymerases can be subdivided into seven different families: A, B, C, D, X, Y, and RT. DNA-dependent DNA polymerases fall into one of six families (A, B, C, D, X, and Y), with most falling into one of three families (A, B, and C). See, e.g., Ito et al. (1991) Nucleic Acids Res. 19:4045-4057; Braithwaite et al. (1993) Nucleic Acids Res. 21:787-802; Filee et al. (2002) J. Mol.

Evol. 54:763-773; and Alba (2001) Genome Biol. 2:3002.1-3002.4. Certain DNA polymerases may be single-chain polypeptides (e.g., certain family A and B polymerases) or multi-subunit enzymes (e.g., certain family C polymerases) with one of the subunits having polymerase activity. Id. A fusion protein may comprise a DNA polymerase selected from a family A, B, C, D, X, or Y polymerase.

There are five known DNA polymerases in bacteria. All have 5'-3' polymerase activity and include Pol I, Pol II, Pol III, Pol IV and Pol V. Pol IV and Pol V are Y-family DNA polymerases, known to have weak fidelity on normal templates and can replicate through damaged DNA. Pol I, Pol II and Pol III all have 3'-5' exonuclease activity while Pol I is also implicated in DNA repair, having both 5'-3' polymerase and 3'-5' proofreading exonuclease activity.

Family A polymerases ("Pol A") include both replicative and repair polymerases. Replicative members from this family include T7 DNA polymerase and the eukaryotic mitochondrial DNA Polymerase γ. Among the repair polymerases are *E. coli* DNA Pol I, *Thermus aquaticus* Pol I (Taq DNA polymerase), and *Bacillus stearothermophilus* Pol I. Excision repair and processing of Okazaki fragments generated during lagging strand synthesis are performed by the repair polymerases. Because most thermostable Pol A enzymes do not possess the 3' to 5' exonuclease activity, they are incapable of proofreading the newly synthesized nucleic acid strand and consequently have high error rates.

Family B polymerases ("Pol B") are substantially replicative polymerases including the major eukaryotic DNA polymerases α, δ, ε, and also DNA polymerase ζ. Pol B polymerases also include DNA polymerases encoded by some bacteria and bacteriophages, of which the best characterized are from T4, Phi29 and RB69 bacteriophages. Pol B enzymes are involved in both leading and lagging strand synthesis and are noteworthy for their remarkable accuracy during replication as many have strong 3'-5' exonuclease activity the exceptions being DNA polymerase α and ζ which lack proofreading activity.

In certain embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

PCR amplification time can be decreased significantly by changing the enzyme used. Three key intrinsic properties of a DNA polymerase play important roles in determining the overall reaction time required for the PCR amplification. The first property is "elongation rate" (or "extension rate"), which is defined as the number of nucleotides polymerized per second per molecule of DNA polymerase. The second property is "processivity", which is defined as the average number of nucleotides added by a DNA polymerase in a single binding event. Both "elongation rate" and "processivity" depend on the components of the reaction media and on the DNA template sequence. The third property is the presence or absence of terminal transferase activity, which is the non-templated addition of a single nucleotide, mainly adenosine, to the 3' end of the amplified DNA strand.

Considerations to for reducing PCR time can start with evaluation of the polymerase enzyme used. For example, the mechanism for enzyme activation can decrease PCR time by about 10 minutes. Hot start enzymes with chemical modifications such as AmpliTaq Gold® DNA polymerase (Applied Biosystems, Foster City, Calif.), can require an eight to eleven minute heat activation step while hot start enzymes having antibody (Platinum® Taq DNA Polymerase, Invitrogen, Carlsbad, Calif., SpeedSTAR™ HS DNA Polymerase, Takara, Madison, Wis.), oligonucleotide, or use of single-stranded binding proteins to primers can reduce the hot start mechanism to one to two minutes.

Improvements which decrease the denaturation, annealing and extension times can further reduce PCR time by use of a more processive DNA polymerase as well as utilization of a thermal cycler with faster ramping rates or changing from a 3-step cycling protocol to a 2-step protocol which removes one ramping time per PCR cycle. Further, use of a Pol B DNA polymerase can eliminate the need for a final extension step, saving up to 60 minutes. However, use of a variety of Pol B family DNA polymerases has been shown to produce higher stutter peak heights making STR profile interpretation difficult (data not shown).

In some embodiments, envisioned are Pol A and Pol B DNA polymerases for amplifying a target nucleic acid sequence in under at least 50 minutes, under at least 45 minutes, under at least 40 minutes, under at least 35 minutes, under at least 30 minutes, under at least 25 minutes and under at least 20 minutes. The resulting amplification product can be detected. In some embodiments the detection is selected from microfluidics, electrophoresis, mass spectrometry and the like known to one of skill in the art for detecting amplification products.

In some embodiments, PCR amplification products may be detected by fluorescent dyes conjugated to the PCR amplification primers, for example as described in PCT patent application WO 2009/059049. PCR amplification products can also be detected by other techniques, including, but not limited to, the staining of amplification products, e.g. silver staining and the like.

In some embodiments, detecting comprises an instrument, i.e., using an automated or semi-automated detecting means that can, but need not, comprise a computer algorithm. In some embodiments, the instrument is portable, transportable or comprises a portable component which can be inserted into a less mobile or transportable component, e.g., residing in a laboratory, hospital or other environment in which detection of amplification products is conducted. In certain embodiments, the detecting step is combined with or is a continuation of at least one amplification step, one sequencing step, one isolation step, one separating step, for example but not limited to a capillary electrophoresis instrument comprising at least one fluorescent scanner and at least one graphing, recording, or readout component; a chromatography column coupled with an absorbance monitor or fluorescence scanner and a graph recorder; a chromatography column coupled with a mass spectrometer comprising a recording and/or a detection component; a spectrophotometer instrument comprising at least one UV/visible light scanner and at least one graphing, recording, or readout component; or a microarray with a data recording device such as a scanner or CCD camera. In certain embodiments, the detecting step is combined with an amplifying step, for example but not limited to, real-time analysis such as Q-PCR. Exemplary means for performing a detecting step include the ABI PRISM® Genetic Analyzer instrument series, the ABI PRISM® DNA Analyzer instrument series, the ABI PRISM® Sequence Detection Systems instrument series, and the Applied Biosystems Real-Time PCR instrument series (all from Applied Biosystems); and microarrays and related software such as the Applied Biosystems microarray and Applied Biosystems 1700 Chemiluminescent Microarray Analyzer and other commercially available microarray and analysis systems available from Affymetrix, Agilent, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, and Genotyper® software (all from Applied Biosystems).

In some embodiments, an amplification product can be detected and quantified based on the mass-to-charge ratio of at least a part of the amplicon (m/z). For example, in some embodiments, a primer comprises a mass spectrometry-compatible reporter group, including without limitation, mass tags, charge tags, cleavable portions, or isotopes that are incorporated into an amplification product and can be used for mass spectrometer detection (see, e.g., Haff and Smirnov, Nucl. Acids Res. 25:3749-50, 1997; and Sauer et al., Nucl. Acids Res. 31:e63, 2003). An amplification product can be detected by mass spectrometry. In some embodiments, a primer comprises a restriction enzyme site, a cleavable portion, or the like, to facilitate release of a part of an amplification product for detection. In certain embodiments, a multiplicity of amplification products are separated by liquid chromatography or capillary electrophoresis, subjected to ESI or to MALDI, and detected by mass spectrometry. Descriptions of mass spectrometry can be found in, among other places, The Expanding Role of Mass Spectrometry in Biotechnology, Gary Siuzdak, MCC Press, 2003.

In some embodiments, detecting comprises a manual or visual readout or evaluation, or combinations thereof. In some embodiments, detecting comprises an automated or semi-automated digital or analog readout. In some embodiments, detecting comprises real-time or endpoint analysis. In some embodiments, detecting comprises a microfluidic device, including without limitation, a TaqMan® Low Density Array (Applied Biosystems). In some embodiments, detecting comprises a real-time detection instrument. Exemplary real-time instruments include, the ABI PRISM® 7000 Sequence Detection System, the ABI PRISM® 7700 Sequence Detection System, the Applied Biosystems 7300 Real-Time PCR System, the Applied Biosystems 7500 Real-Time PCR System, the Applied Biosystems 7900 HT Fast Real-Time PCR System (all from Applied Biosystems); the LightCycler™ System (Roche Molecular); the Mx3000P™ Real-Time PCR System, the Mx3005P™ Real-Time PCR System, and the Mx4000® Multiplex Quantitative PCR System (Stratagene, La Jolla, Calif.); and the Smart Cycler System (Cepheid, distributed by Fisher Scientific). Descriptions of real-time instruments can be found in, among other places, their respective manufacturer's users manuals; McPherson; DNA Amplification: Current Technologies and Applications, Demidov and Broude, eds., Horizon Bioscience, 2004; and U.S. Pat. No. 6,814,934.

Those in the art understand that the detection techniques employed are generally not limiting. Rather, a wide variety of detection means are within the scope of the disclosed methods and kits, provided that they allow the presence or absence of a microorganism in the sample to be determined.

In various embodiments of the present teachings it has been discovered that use of a two-step amplification cycle in a PCR cycling protocol can reduce the PCR time to under 45 min. while obtaining a complete, interpretable STR profile using 1 ng of control DNA 9947A. Examples of Fast PCR protocols with Pol A family enzymes are illustrated in Table 1.

TABLE 1

| Fast PCR Protocols with Pol A DNA Polymerases | | | | |
|---|---|---|---|---|
| STR Kit: | Identifiler ® Plus | | Identifiler ® Plus | |
| Enzyme: | AmpliTaq Gold ® DNA Polymerase | | Platinum ® Taq DNA Polymerase | |
| PCR Protocol | | No. of Amplification cycles | | No. of Amplification cycles |
| Template Denaturation | 95° C./11 min. | | 95° C./1 min. | |
| Amplification cycle | 94° C./5 sec. 59° C./20 sec. | 29X | 94° C./5 sec. 59° C./20 sec. | 29X |
| Nontemplate Adenylation | 72° C./1 min. | | 72° C./1 min. | |
| Total PCR Time: | 45 min. | | 36.5 min. | |

In some embodiments the two-step amplification cycle is 30 seconds or less, 25 seconds or less, 20 seconds or less, 15 seconds or less or 10 seconds or less. In some embodiments the amplification cycle is carried our at least 25 times, at least 26 times, at least 27 times, at least 28 times or at least 30 times.

In some embodiments, the predicted Tm of the primers is 5° C. less than the annealing temperature, 10° C. less than the annealing temperature, or 15° C. less than the annealing temperature. Likewise, the annealing temperature in the amplification cycle can be 5° C. greater than the annealing temperature, 10° C. greater than the annealing temperature, or 15° C. greater than the annealing temperature. The Tm is a reflection of the temperature that double-stranded DNA becomes single-stranded.

In various embodiments of the present teachings the annealing temperature and the elongation temperature are identical and the extending of primer annealed to the template occurs at the annealing temperature, for example, but not limited to, the two-step amplification cycling protocol. In some embodiments the annealing temperature is from about 55° C. to about 75° C., and from about 57° C. to about 72° C., from about 58° C. to about 72° C., from about 59° C. to about 72° C. and from about 60° C. to about 72° C. In some embodiments the reaction mixture undergoing PCR amplification is held at the annealing temperature for 5 seconds or less, 4 seconds or less, 3 seconds or less, 2 seconds or less or 1 second or less.

In various embodiments of the present teaching the denaturing temperature, the temperature at which the double-stranded deoxyribonucleotide separates into single strands, occurs at a denaturing temperature sufficient to denature the double-stranded nucleic acid such as at from about 85° C. to about 100° C. and the reaction mixture is held at the denaturing temperature for 9 seconds or less, 8 seconds or less, 7 seconds or less, 6 seconds or less, 5 seconds or less, 4 seconds or less, 3 seconds or less, 2 seconds or less or 1 second and the annealing/elongation temperature is 30 seconds or less, 25 seconds or less, 20 seconds or less, 15 seconds or less, 10 seconds or less or 5 seconds or less.

In various embodiments the temperature of denaturing, annealing/elongation and extension reflect the temperature of the heating element or heat block within the thermal cycler or a microfluidic device. In other embodiments the temperatures of denaturing, annealing/elongation and extension reflect the temperature of the reaction mixture. The reaction mixture, once it reaches the denaturing and/or annealing/elongation temperature is not required to be held at the denaturing and/or annealing/elongation temperature once the denaturing and/or annealing/elongation temperature is reached by the reaction mixture.

In various embodiments of the present teachings the Pol A enzyme can be an enzyme derived from *Thermus aquaticus, Thermus thermophilus* HB-8 or HB-27, *Thermus flavus, Thermus maritime*; large fragment, *Thermotoga naepolitana, Thermococcus gorgonarius, Thermococcus litoralis, Thermococcus aggregans*, and *Thermomicrobium roseum*. The Pol A family polymerase can be a fragment, variant or recombinant form of the thermostable DNA polymerase. Such fragments, variants or recombinant forms that retain their DNA polymerase activity are well known to one of skill in the art.

In various embodiments of the present teachings it has been discovered that high concentrations of a Pol A enzyme along with high concentrations of primers unexpectedly and substantially reduce PCR amplification times for obtaining complete, interpretable STR profiles. Titrating the selected Pol A enzyme to slowly increase the enzyme in the reaction mix was performed to identify the optimal concentration (Example A). Contrary to the studies of Vallone et al. (Forensic Sci. Intl.: Gen. 3:42-45 2008) and Giese et al. (J. Forensic Sci. 54(6): 1287-1296, 2009), successful amplification for the determination of an STR profile of a nucleic acid sample is dependent not only on the level of Pol A enzyme, but the level of primer concentration and required no added enzymes or supplements.

Figure 1B:
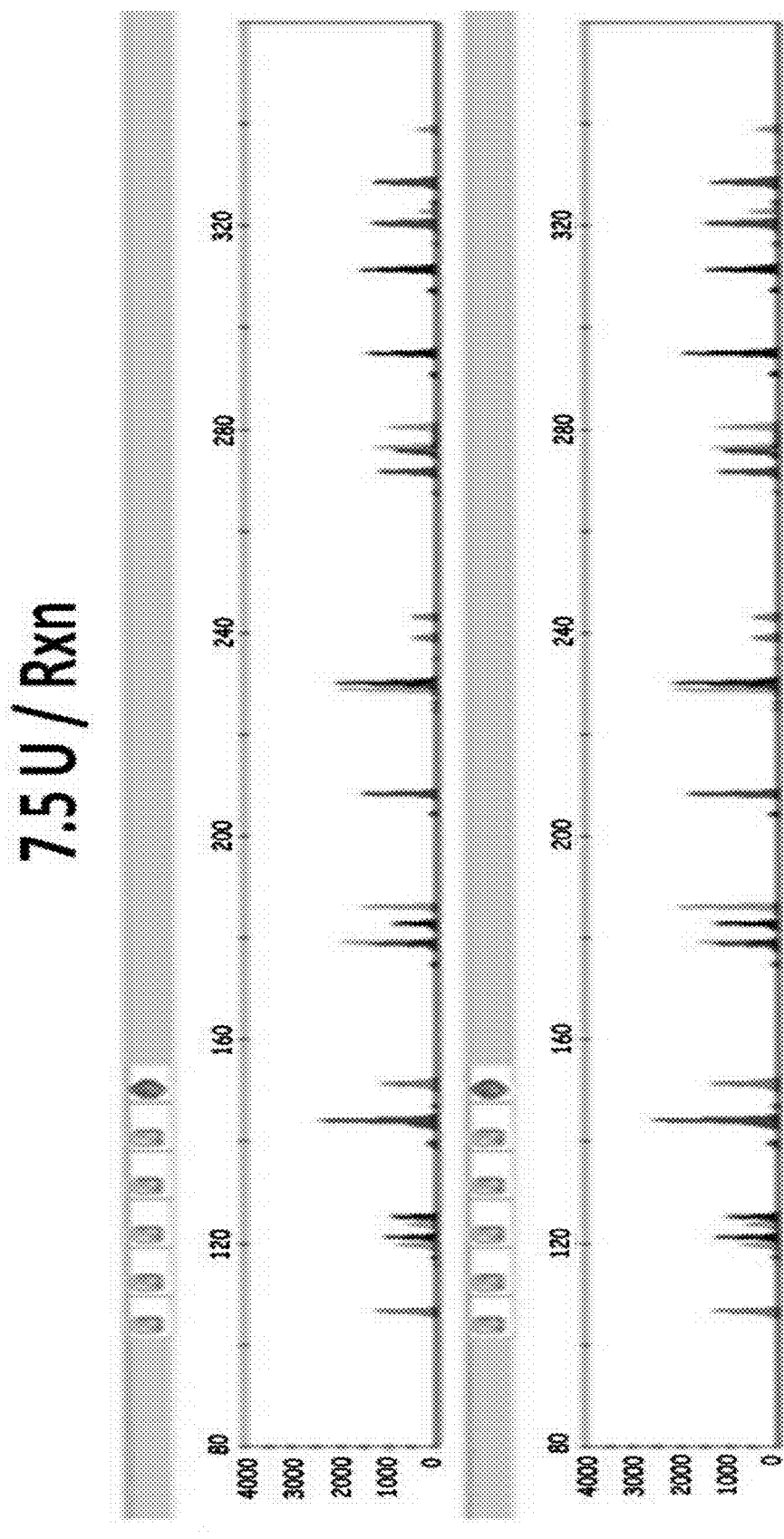
Figure 1C:
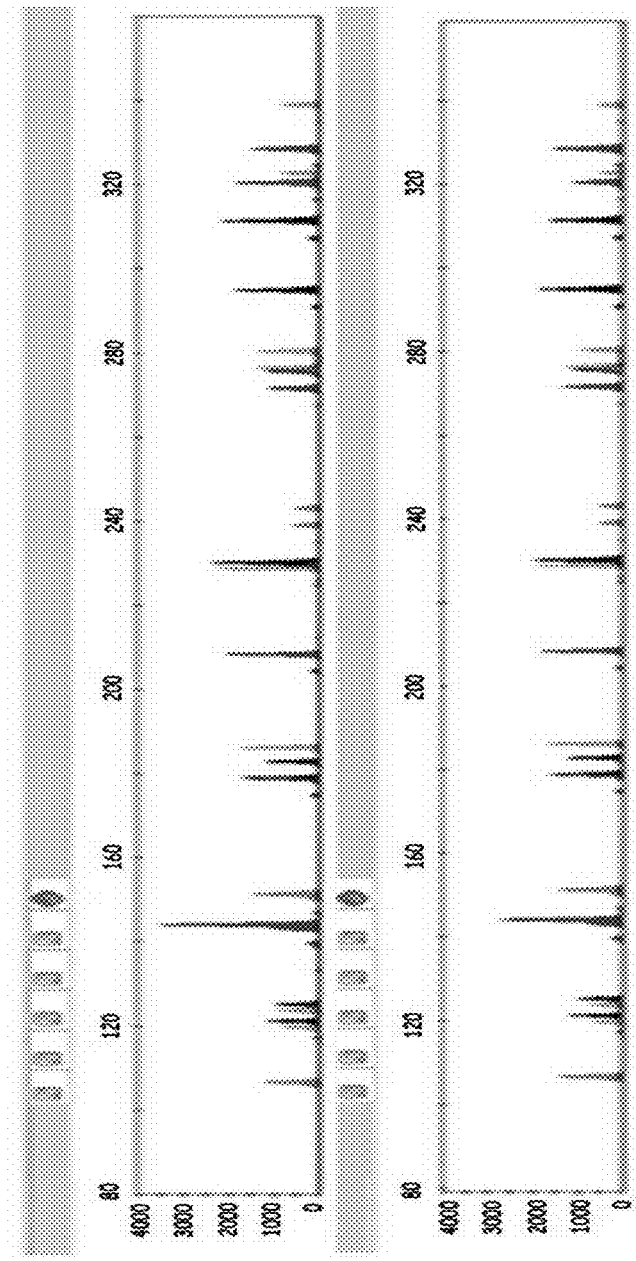
Figure 1D:
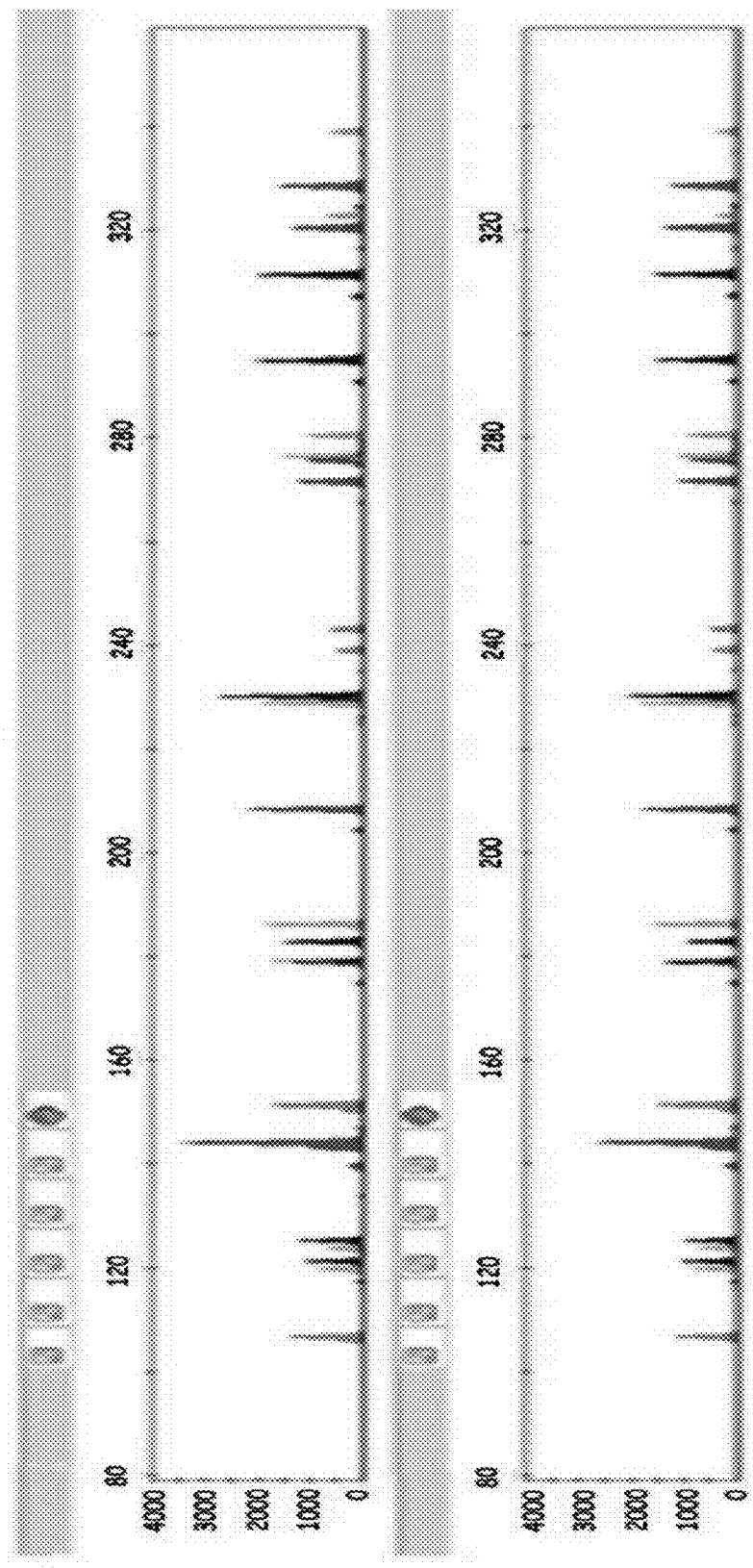
Figure 1E:
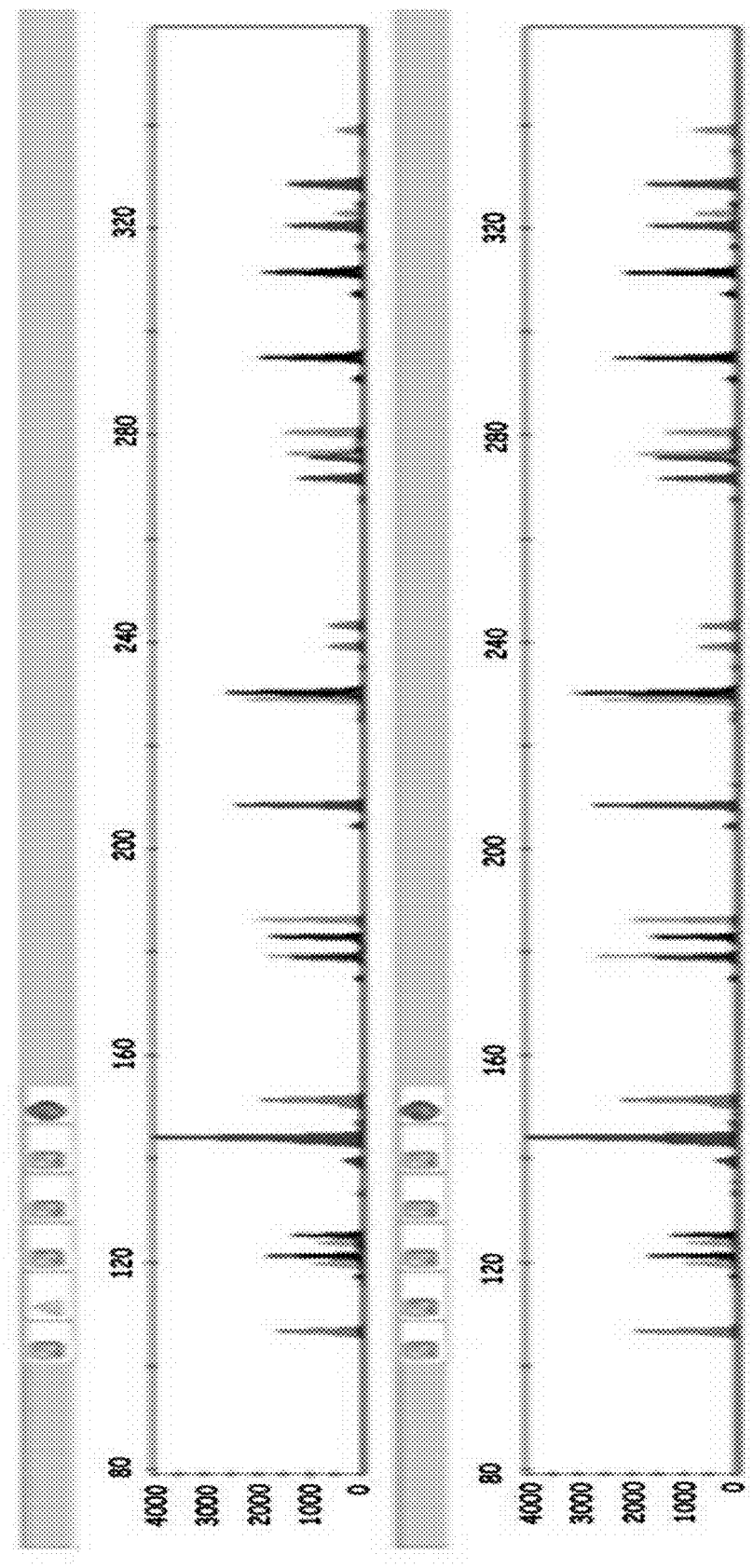

Using the AmpF/STR® Identifiler Plus® PCR Amplification Kit (Applied Biosystems, Foster City, Calif.), for the primers and substituting Platinum® Taq in the Master Mix, the concentration of the Pol A enzyme, Platinum® Taq, was increased incrementally as shown in FIGS. 1A-1E. Amplification was performed in an Applied Biosystems GeneAmp® 9700 PCR instrument (Table 1). Unexpectedly, insufficient enzyme resulted in incomplete STR profiles (FIG. 1A), e.g., D5 and enzyme in excess resulted in split peak morphologies (FIGS. 1D and 1E, ~140-160 bp), particularly in the D5 and D8 loci. Surprisingly, a full, interpretable STR profile was obtained using the Fast PCR protocol and Platinum Taq enzyme (FIGS. 1B to 1C).

Studies to compare the sensitivities of AmpliTaq Gold®, Platinum® Taq and SpeedSTAR™ enzymes with the Fast PCR protocol verse the Identifiler Plus kit and standard PCR protocol showed that the standard protocol was able to detect a complete STR profile with as little as 125 pg of input DNA while the Fast PCR protocol achieved a complete STR profile down to 500 ng DNA with AmpliTaq Gold and 250 pg DNA for Platinum and SpeedSTAR. As would be expected, the average peak height was larger with the standard protocol verses the Fast PCR protocol (data not shown).

Specificity studies indicated higher cross-species reactivity with Platinum and SpeedSTAR enzymes with the Fast PCR protocol verse AmpliTaq Gold enzyme. Additionally, when compared to the standard protocol, inhibition of PCR when the Fast PCR protocol was followed was present with as little as 100 uM Hematin and 25 ng/ul Humic acid for AmpliTaq Gold enzyme, 200 uM Hematin and 50 ng/ul Humic acid for Platinum enzyme and 200 uM Hematin and 75 ng/ul Humic acid for SpeedSTAR enzyme. These results can be reversed by increasing the cycle number or optimization of the master mix formulation.

In various embodiments of the present teachings the family A polymerase can be a bacterial polymerase or a fragment or variant of a bacterial family A polymerase having polymerase activity. The thermostable polymerase can also be a recombinant polymerase, a fragment or variant of a recombinant DNA polymerase that has polymerase activity. In some embodiments the polymerase is a variant of a Taq DNA polymerase with increased processivity relative to naturally occurring Taq DNA polymerase.

In various embodiments the polymerase used in the Fast PCR protocol PCR reaction mixture can further have an indicator molecule to indicate the amount of nucleic acid in the reaction mixture. In some embodiments the indicator molecule can be an indicator probe capable of hybridizing to the double-stranded nucleic acid such as in a 5' nuclease reaction as would be known to one of skill in the art. The probe can be a 5' nuclease probe, a molecular beacon, a PNA probe or other probe known to one of skill in the art.

The present teachings are also directed to kits for determining an STR profile that utilize the methods described above. In some embodiments, a basic kit can comprise a container having at least one pair of oligonucleotide primers capable of amplifying an STR locus. A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers.

Those in the art understand that the detection techniques employed are generally not limiting. Rather, a wide variety of detection means are within the scope of the disclosed methods and kits, provided that they allow the presence or absence of an amplicon to be determined.

Examples

A. Enzyme Titration

A basic PCR buffer solution in bulk was prepared without enzyme having 10-50 mM Tris-HCl, pH 8.0, 1-70 mM of KCl, and $MgCl_2$, 0.15-0.4 mM of each dNTP, 0.4-0.8% Tween 20, optionally 0.05%-1% Triton-x100, 700-3000 ng BSA, 1-8% Glycerol, 0.008-0.05% Sodium azide, optionally 0.5%-2% DMSO, and 1 ng control DNA 9947A for a 25 ul reaction. Aliquots of the PCR buffer were prepared with varying amounts of Platinum Taq DNA polymerase from 1 to 15 units/25 ul PCR reaction, in duplicate, (FIGS. 1A-1E). The Fast PCR protocol in Table 1 was followed in conjunction with the primers used in the Identifiler Plus Kit being added to the reaction mix. The amplification products were loaded on an Applied Biosystems 3130xl capillary electrophoresis instrument and analyzed using GeneMapper® ID-X software. Optimal enzyme concentration was determined based on the ability to obtain a complete STR profile with interpretable peak heights overall.

Insufficient enzyme resulted in incomplete STR profiles (FIG. 1A), e.g., D5 and enzyme in excess resulted in split peak morphologies (FIGS. 1D and 1E, ~140-160 bp), particularly in the D5 and D8 loci. Surprisingly, a full, interpretable STR profile was obtained using the Fast PCR protocol and Platinum Taq enzyme (FIGS. 1B to 1C).

B. Primer Titration

Primer concentration also appeared to impact the success of the Fast PCR protocol for the Identifiler® Direct and NGM™ Kits (Applied Biosystems) (data not shown). Thus, all primer concentrations were adjusted to ≥0.100 uM in a 25 ul reaction mix. PCR was performed according to the Fast PCR protocol in Table 1 and evaluated as described for Enzyme Titration.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

We claim:

1. A method comprising subjecting a reaction mixture to at least one amplification cycle, wherein the reaction mixture comprises a double-stranded nucleic acid, at least 15 primer pairs wherein each primer pair is capable of annealing to a different short tandem repeat (STR) locus, wherein the amplification cycle is a two step amplification, and wherein the extension occurs at the annealing temperature and thereby detecting a complete STR profile.

2. The method of claim 1, wherein the time to complete one amplification cycle is 25 seconds or less.

3. The method of claim 1, wherein the annealing temperature is at least about 5° C. greater than the predicted Tm of at least one of the primers.

4. The method of claim 3, wherein the annealing temperature is from about 55° C. to about 75° C.

5. The method of claim 1, wherein the reaction mixture is held at the annealing temperature for 1 second or less.

6. The method of claim 1, wherein the reaction mixture comprises a Family A polymerase.

7. The method of claim 6, wherein the Family A polymerase comprises a polymerase from *Thermus aquaticus, Thermus thermophilus* HB-8, *Thermus thermophilus* HB-27, *Thermus flavus, Thermus maritime*; large fragment, *Thermotoga naepolitana, Thermococcus gorgonarius, Thermococcus litoralis, Thermococcus aggregans*, or *Thermomicrobium roseum*.

8. The method of claim 1, further comprising at least one primer pair capable of annealing to complementary strands of the double-stranded nucleic acid and amplifying a region of the amelogenin locus.

9. The method of claim 8, wherein said amplified amelogenin locus is found on X chromosome and on Y chromosome.

10. The method of claim 1, comprising at least 40 primers capable of annealing to complementary strands of the double-stranded nucleic acid and amplifying at least 20 short tandem repeat (STR) loci.

11. The method of claim 1, wherein the thermostable DNA polymerase comprises a bacterial family A polymerase or a fragment or variant of a bacterial family A polymerase having polymerase activity.

12. The method of claim 1, wherein the reaction mixture is subjected to up to 40 amplification cycles.

13. The method of claim 1, wherein the number of amplified molecules produced in at least one of the at least one amplification cycle is from 1.6-fold to 2-fold the number of molecules present at the start of the at least one of the at least one amplification cycle.

14. The method of claim 1, wherein the amplification efficiency of polymerase in at least one of the at least one amplification cycle is from 0.8 to 1.0.

15. The method of claim 1 wherein the amplification cycle occurs in a thermocycler instrument comprising a sealed tube, a lid and a block, wherein the sealed tube is in physical contact with the lid and the block and both the lid and block can be heated above ambient temperature.

16. The method of claim 1, wherein the amplification cycle occurs in a sealed tube with an internal volume of at least 0.2 ml.

* * * * *